United States Patent [19]

Mouzin et al.

[11] Patent Number: 4,478,836

[45] Date of Patent: Oct. 23, 1984

[54] 1-ARYL 2-AMINOMETHYL CYCLOPROPANE CARBOXYAMIDE (Z) DERIVATIVES AND THEIR USE AS USEFUL DRUGS IN THE TREATMENT OF DISTURBANCES OF THE CENTRAL NERVOUS SYSTEM

[75] Inventors: Gilbert Mouzin; Henri Cousse; Bernard Bonnaud, all of Castres; Michel Morre, Toulouse; Antoine Stenger, Castres, all of France

[73] Assignee: Pierre Fabre S.A., Castres, France

[21] Appl. No.: 390,810

[22] Filed: Jun. 22, 1982

[30] Foreign Application Priority Data

Jun. 23, 1981 [FR] France ................................ 81 12312

[51] Int. Cl.$^3$ .................. C07L 103/82; A61K 31/165
[52] U.S. Cl. .......................... 424/248.54; 260/501.18; 544/130; 544/141; 544/165; 544/169; 546/189; 546/208; 546/245; 548/524; 548/539; 548/567; 548/578; 564/163; 564/164; 564/165; 564/166; 564/167; 564/171; 564/174; 424/248.57; 424/267; 424/274; 424/316; 424/324
[58] Field of Search ............... 564/164, 174, 165, 166, 564/167, 171; 260/501.18; 544/130, 141, 165, 169; 546/189, 208, 245; 548/539, 524, 567, 578; 424/248.54, 248.57, 267, 274, 316, 324

[56] References Cited

U.S. PATENT DOCUMENTS 3,989,722 11/1976 Cognacq ............................. 564/164

FOREIGN PATENT DOCUMENTS 570688 2/1959 Canada .............................. 564/164
619080 4/1961 Canada .............................. 560/164

OTHER PUBLICATIONS

"Hackh's Chemical Dictionary" 4th Ed, p. 35, (1969) Edit by J. Grant.
Casadio, Boll. Chim. Farm., 117 pp. 331–342, (1978).
Wilson, "Textbook of Organic Medicinal and Pharmaceutical Chemistry," pp. 63–65, 69, 70, 73, 97–99 & 117–119, (1977, 7th Ed).

Primary Examiner—Michael L. Shippen
Attorney, Agent, or Firm—Gordon W. Hueschen

[57] ABSTRACT

The present invention concerns new derivatives of 1-aryl 2-aminomethyl cyclopropane carboxamides (Z) of general formula I:

in which:
R represents a hydrogen or halogen atom, a lower alkyl group, a lower alkoxy group, or a hydroxy. nitro or amino group;
n represents the value 1 or 2;
$R_1$ and $R_2$ represent a hydrogen atom, a lower alkyl group, an aryl or lower alkaryl group, possibly substituted, preferably in para position, by a halogen atom, preferably a chlorine atom;
$R_1$ and $R_2$ may also form a heterocycle having 5 or 6 members with the adjacent nitrogen atom;
$R_3$ and $R_4$ represent a hydrogen atom or a lower alkyl group;
$R_3$ and $R_4$ may also form with the adjacent nitrogen atom a heterocycle having 5 or 6 members, possibly containing an additional heteroatom selected from among nitrogen and oxygen, as well as their salts with therapeutically acceptable inorganic or organic acids, and their pharmaceutical compositions and use in the treatment of central nervous system disturbances, e.g., depression.

16 Claims, No Drawings

1-ARYL 2-AMINOMETHYL CYCLOPROPANE CARBOXYAMIDE (Z) DERIVATIVES AND THEIR USE AS USEFUL DRUGS IN THE TREATMENT OF DISTURBANCES OF THE CENTRAL NERVOUS SYSTEM

The present invention (made at the Pierre Fabre Research Center) concerns new 1-aryl 2-aminomethyl cyclopropane carboxamide derivatives (Z), their method of preparation and their use in therapy and in particular in the treatment of disturbances of the central nervous system.

The closest known prior art can be illustrated, for instance, by the applicant's French Pat. No. 75 07120, covering a method of preparing 1-aryl 2-hydroxymethyl cyclopropane carboxylic acids.

These acid-alcohol derivatives are furthermore the subject of an article by G. Mouzin, H. Cousse and B. Bonnaud in Synthesis 1978, 304, reprinted in Synthetic Methods of Organic Chemistry (Edited by W. Theilheimer) 34,1980,317.

The pharmacological study of the derivatives of 1-phenyl 2-hydroxymethyl cyclopropane carboxylic acid which has been described by S. Casadio, B. Bonnaud. G. Mouzin and H. Cousse in Boll. Chim. Farm. 117, 1978, 331, has shown the low pharmacological activity of these derivatives.

The present invention relates to compounds which differ from those of the said prior art; there are concerned amino cyclopropane amides having the general formula

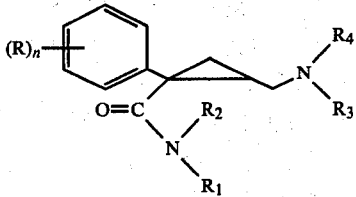

It has, as a matter of fact, been shown that certain modulations effected on the functional groups borne by the cyclopropane group confer upon these new amino cyclopropane amides very interesting pharmacological properties and, more particularly, a very definite antidepressant action which makes it possible to use these compounds in therapy for the treatment of disturbances of the central nervous system.

The present invention concerns new derivatives of 1-aryl 2-aminomethyl cyclopropane carboxamides (Z) of general formula I:

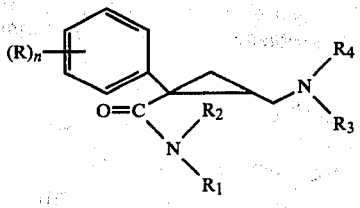

in which:
R represents a hydrogen or halogen atom, a lower alkyl, lower alkoxy, hydroxy, nitro or amino group;

n represents the values 1 or 2;

$R_1$ and $R_2$ represent a hydrogen atom, a lower alkyl group or an aryl or lower alkylaryl group, which may possibly be substituted, preferably in para position, by a halogen atom, preferably a chlorine atom;

$R_1$ and $R_2$ possibly forming a heterocycle having 5 or 6 members with the adjacent nitrogen atoms;

$R_3$ and $R_4$ represent a hydrogen atom or a lower alkyl group;

$R_3$ and $R_4$ possibly also forming with the adjacent nitrogen atom a heterocycle having 5 or 6 members, possibly containing an additional heteroatom selected from among nitrogen and oxygen.

The present invention also concerns the salts of the compounds of general formula I with therapeutically acceptable inorganic or organic acids.

By way of illustration and not of limitation of these salts mention may be made of the hydrohalides, such as hydrochloride, fumarate, maleate, oxalate, citrate and glutamate.

In the present specification the lower alkyl radicals and the lower alkyl fragments of the alkylaryl and alkoxy radicals designate linear or branched hydrocarbon chains containing from one to four carbon atoms, inclusive.

The present invention also concerns a method of preparing compounds of general formula I which consists in hydrolyzing an amino ester of general formula (II) in order to obtain an amino acid of general formula (III).

The said amino acid of general formula (III) in its turn is transformed into the corresponding halide of general formula (IV) by means of a thionyl halide. The halide of general formula (IV) is then condensed on an amine.

The method of preparation in accordance with the present invention can be illustrated by the following reaction mechanism:

REACTION MECHANISM

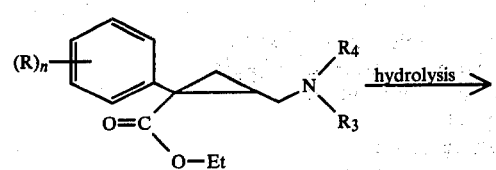

(II)

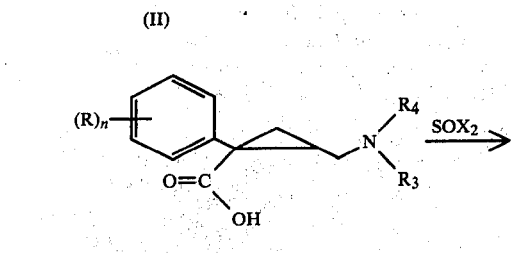

(III)

-continued

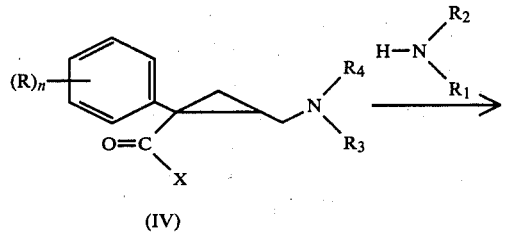

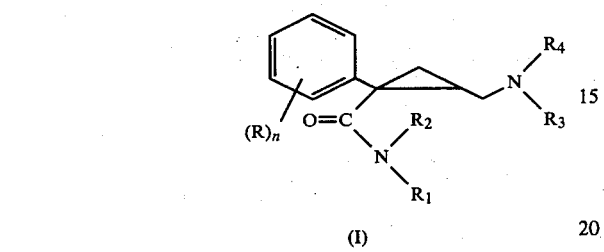

X represents a halogen atom and
R, $R_1$, $R_2$, $R_3$, $R_4$ and n have the meanings given previously in connection with general formula I.

The following examples illustrate the invention without, of course, limiting its scope.

EXAMPLE 1

Preparation of 1-phenyl 1-aminocarbonyl 2-dimethylamino methyl cyclopropane (Z)

(a) hydrochloride of 1-phenyl 1-carboxy 2-dimethylamino methyl cyclopropane (Z)

To a solution of 21.15 g of 1-phenyl 1-ethoxycarbonyl 2-dimethylaminomethyl cyclopropane (Z) hydrochloride in 200 cc of ethanol there are added 180 cc of caustic soda (N). The solution is heated under reflux for four hours and then neutralized by the addition of 105 cc of hydrochloric acid (N). The solution is evaporated to dryness, taken up with ethanol, and the hydrochloride precipitated by the addition of ethyl ether.

The product of the formula

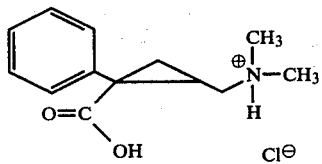

is recovered in a yield of 85%.
Empirical formula: $C_{13}H_{18}ClNO_2$
Molecular weight: 255.7
Crystals: white
Melting point: 200° C.
Plate chromatography:
  support: silica gel 60 F 254 Merck
  solvent: butanol/acetic acid/water 6/2/2
  development: UV and iodine
  Rf: 0.33

(b) Hydrochloride of 1-phenyl 1-chlorocarbonyl 2-dimethylaminomethyl cyclopropane (Z)

A mixture of 17.5 g of 1-phenyl 1-carboxydimethylaminomethyl cyclopropane (Z) hydrochloride in 26 cc of thionyl chloride is maintained under agitation at room temperature for 12 hours. 150 cc of ethyl ether are then added; the product crystallizes and the product of the formula

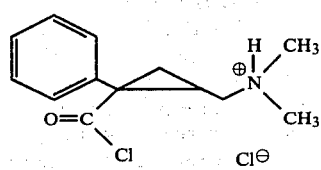

is recovered in a yield of 95%.
Empirical formula: $C_{13}H_{17}Cl_2NO$
Molecular weight: 274.2
Crystals: white
Melting point: 135° C.

(c) 1-phenyl 1-aminocarbonyl 2-dimethylaminomethyl cyclopropane (Z)

5.48 g of 1-phenyl 2-dimethylaminomethyl cyclopropane (Z) hydrochloride are introduced with agitation at room temperature into 15 cc of 20% ammonia and are then maintained for four hours at rocyclopropane (Z)

5.48 g of 1-phenyl 2-dimethylaminomethyl cyclopropane (Z) hydrochloride are introduced with agitation at room temperature into 15 cc of 20% ammonia and are then maintained for four hours at room temperature. After the customary treatments, the product of the formula:

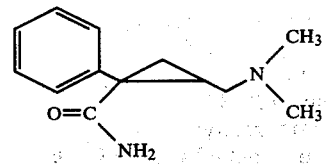

is recovered in a yield of 75% by recrystallization from petroleum ether.
Empirical formula: $C_{13}H_{18}N_2O$
Molecular weight: 218.29
Crystals: white
Melting point: 84° C.
Plate chromatography:
  support: silica gel 60 F 254 Merck
  solvent: chloroform/methanol/ammonia 80/18/2
  development: UV and iodine
  Rf: 0.44
IR spectrum (KBr): $\delta C=O$ 1670 cm$^{-1}$.

EXAMPLE 2

Preparation of 1-phenyl 1-dimethylamino carbonyl 2-dimethylamino methyl cyclopropane (Z)

In a manner similar to that described in Example 1, but using dimethylamine and salifying with hydrochloric acid, there is obtained the product of formula:

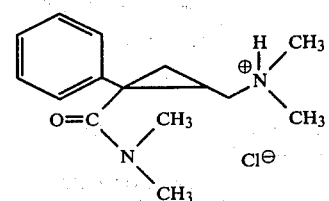

Empirical formula: $C_{15}H_{23}ClN_2O$
Molecular weight: 282.8
Crystals: white
Melting point: 210° C.
Plate chromatography:
   support: silica gel 60 F 254 Merck
   solvent: chloroform/methanol/ammonia 80/18/2
   development: UV and iodine
   Rf: 0.52
IR spectrum (KBr): $\delta C=O$ 1630 cm$^{-1}$.

EXAMPLE 3

1-Phenyl 1-ethylaminocarbonyl 2-dimethylamino methyl cyclopropane (Z) maleate

In a manner similar to that described in Example 1, but using ethylamine and maleic acid as salifying agent, the product of formula:

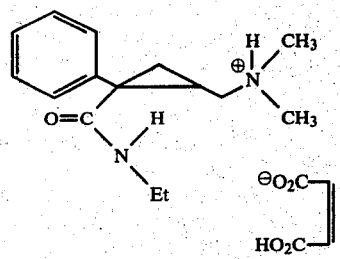

is obtained.
Empirical formula: $C_{19}H_{26}N_2O_5$
Molecular weight: 362.4
Crystals: white
Melting point: 105° C.
Plate chromatography:
   support: silica gel 60 F 254 Merck
   solvent: chloroform/methanol/ammonia 80/18/2
   development: UV and iodine
   Rf: 0.58
IR spectrum (KBr): $\delta C=O$ (amide) 1645 cm$^{-1}$.

EXAMPLE 4

1-Phenyl 1-diethylaminocarbonyl 2-amino methyl cyclopropane (Z) hydrochloride

In a manner similar to that described in Example 1, but hydrolyzing the hydrochloride of 1-phenyl 1-ethoxycarbonyl 2-aminomethyl cyclopropane (Z) and then treating the intermediate acid chloride with diethylamine and salifying with hydrochloric acid, the product of formula:

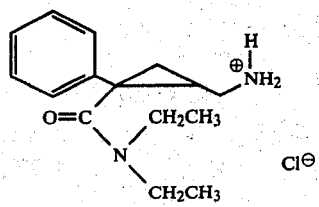

is obtained.
Empirical formula: $C_{15}H_{23}ClN_2O$
Molecular weight: 282.8
Crystals: white
Melting point: 180° C.
Plate chromatography:
   support: silica gel 60 F 254 Merck
   solvent: butanol/acetic acid/water 6/2/2
   development: UV and iodine
   Rf: 0.44
IR Spectrum (KBr): $\delta C=O$ 1620 cm$^{-1}$.

EXAMPLE 5

Preparation of 1-phenyl 2-dimethylaminomethyl N-(4'-chlorophenyl) cyclopropane carboxamide (Z) hydrochloride In a manner similar to that described in Example 1, but using parachloroaniline and salifying with hydrochloric acid, one obtains the product of the formula

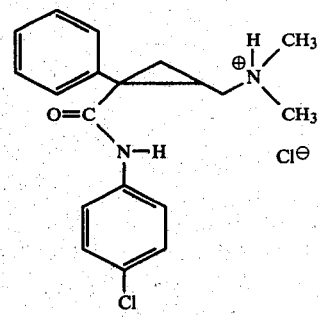

Empirical formula: $C_{19}H_{22}Cl_2N_2O$
Molecular weight: 365.3
Crystals: white
Melting point: 226° C.
Plate chromatography:
   support: silica gel 60 F 254 Merck
   solvent: butanol/acetic acid/water 6/2/2
   development: UV and iodine
   Rf: 0.46
IR spectrum (KBr): $\delta C=O$ 1665 cm$^{-1}$

EXAMPLE 6

Preparation of 1-phenyl 2-dimethylaminomethyl N-(4'-chlorobenzyl) cyclopropane carboxamide (Z) maleate In a manner similar to that described in Example 1, but using parachlorobenzylamine and salifying with maleic acid, one obtains the product of the formula

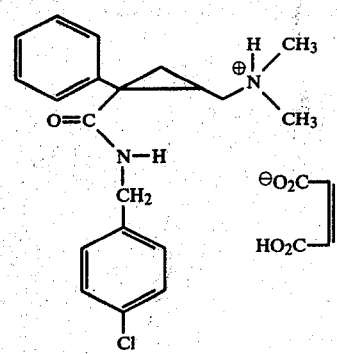

Empirical formula: $C_{24}H_{27}ClN_2O_5$
Molecular weight: 458.9
Crystals: white
Melting point: 110° C.
Plate chromatography:
   support: silica gel 60 F 254 Merck solvent: chloroform/methanol/ammonia 80/18/2
development UV and iodine
Rf: 0.76
IR Spectrum (KBr): δC=O 1640 cm⁻¹ (amide).

EXAMPLE 7

Preparation of 1-phenyl 2-dimethylaminomethyl N-(2-phenyl ethyl) cyclopropane carboxamide (Z) hydrochloride In a manner similar to that described in Example 1, but using 2-phenyl ethylamine and salifying with hydrochloric acid, there is obtained the product of the formula

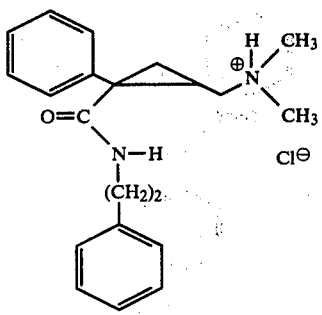

Empirical formula: $C_{21}H_{27}ClN_2O$
Molecular weight: 358.9
Crystals: white
Melting point: 160° C.
Plate chromatography:
    support: silica gel 60 F 254 Merck
    solvent: butanol/acetic acid/water 6/2/2
    development: UV and iodine
    Rf: 0.45
IR Spectrum (KBr): δC=O 1650 cm⁻¹

EXAMPLE 8

Preparation of (3,4-dichloro-1-phenyl) 2-dimethylaminomethyl N,N-dimethyl cyclopropane carboxamide (Z) hydrochloride In a manner similar to that described in Example 1, but using the hydrochloride of 1-(3,4-dichlorophenyl) 1-ethoxycarbonyl 2-dimethylaminomethyl cyclopropane (Z) and then treating the intermediate acid chloride with dimethylamine, there is obtained the product of the formula

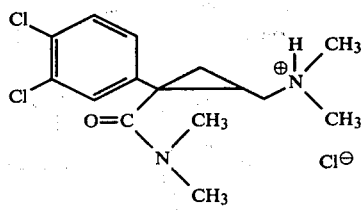

Empirical formula: $C_{15}H_{21}Cl_3N_2O$
Molecular weight: 351.7
Crystals: white
Melting point: 239°–240° C.
Plate chromatography:
    support: silica gel 60 F 254 Merck
    solvent: butanol/acetic acid/water 6/2/2
    development: UV and iodine Rf: 0.27
IR Spectrum (KBr): δC=O 1630 cm⁻¹.

EXAMPLE 9

Preparation of 1-phenyl 1-pyrrolidino carbonyl 2-morpholino methyl cyclopropane (Z) hydrochloride In a manner similar to that described in Example 1, but hydrolyzing the hydrochloride of 1-phenyl 1-ethoxycarbonyl 2-morpholinomethyl cyclopropane (Z) and then treating the intermediate acid chloride with pyrrolidine, there is obtained the product of the formula

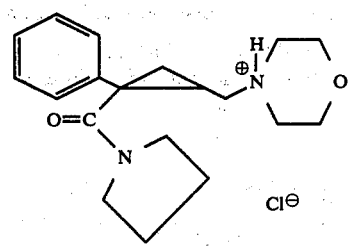

Empirical formula: $C_{19}H_{27}ClN_2O_2$
Molecular weight: 350.9
Crystals: pale yellow
Melting point: 260° C.
Plate chromatography:
    support: silica gel 60 F 254 Merck
    solvent: butanol/acetic acid/water 6/2/2
    development: UV and iodine
    Rf: 0.25
IR Spectrum (KBr): δC=O 1630 cm⁻¹

EXAMPLE 10

Preparation of 1-p-chlorophenyl 1-aminocarbonyl 2-aminomethyl cyclopropane (Z) hydrochloride In a manner similar to that described in Example 1, but hydrolyzing the hydrochloride of 1-p-chlorophenyl 1-ethoxycarbonyl 2-aminomethyl cyclopropane (Z) and then treating the intermediate acid chloride with ammonia and salifying with hydrochloric acid, there is obtained the product of the formula

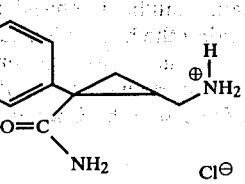

Empirical formula: $C_{11}H_{14}Cl_2N_2O$
Molecular weight: 261.15

EXAMPLE 11

Preparation of 1-orthochlorophenyl 1-aminocarbonyl 2-dimethylamino methyl cyclopropane (Z) hydrochloride In a manner similar to that described in Example 1 but hydrolyzing the hydrochloride of 1-orthochlorophenyl 1-ethoxycarbonyl 2-dimethylaminomethyl cyclopropane (Z) and then treating the intermediate acid chloride with ammonia and salifying with hydrochloric acid, there is obtained the product of the formula

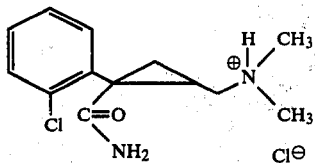

Empirical formula: $C_{13}H_{18}Cl_2N_2O$
Molecular weight: 289.21

EXAMPLE 12

Preparation of 1-p-hydroxyphenyl 1-aminocarbonyl 2-dimethylaminomethyl cyclopropane (Z) hydrochloride In a manner similar to that described in Example 1, but hydrolyzing 1-p-hydroxyphenyl 1-ethoxycarbonyl 2-dimethylaminomethyl cyclopropane (Z) and then treating the intermediate acid chloride with ammonia and salifying with hydrochloric acid, there is obtained the product of the formula

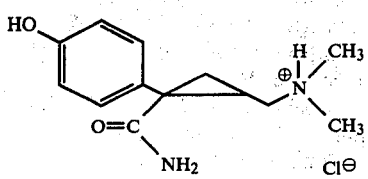

Empirical formula: $C_{13}H_{19}ClN_2O_2$
Molecular weight: 270.76

EXAMPLE 13

Preparation of 1-p-nitrophenyl 1-dimethyl aminocarbonyl 2-dimethylaminomethyl cyclopropane (Z) hydrochloride In a manner similar to that described in Example 1, but hydrolyzing 1-p-nitrophenyl 1-ethoxycarbonyl 2-dimethylamino methyl cyclopropane (Z) and then treating the intermediate acid chloride with dimethylamine and salifying with hydrochloric acid, there is obtained the product of the formula

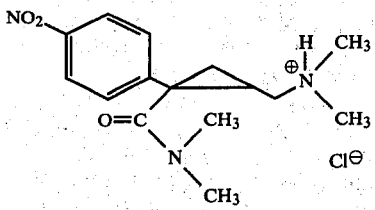

Empirical formula: $C_{15}H_{22}ClN_3O_3$
Molecular weight: 327.8

EXAMPLE 14

Preparation of 1-p-aminophenyl 1-dimethylaminocarbonyl 2-dimethylaminomethyl cyclopropane (Z) hydrochloride In a manner similar to that described in Example 1, but hydrolyzing 1-p-aminophenyl 1-ethoxycarbonyl 2-dimethylaminomethyl cyclopropane (Z) and then treating the intermediate acid chloride with dimethylamine and salifying with hydrochloric acid, there is obtained the product of the formula

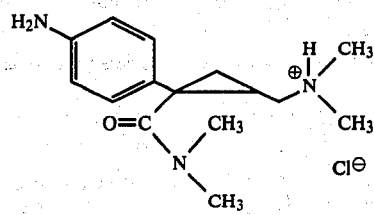

Empirical formula: $C_{15}H_{24}ClN_3O$
Molecular weight: 297.8

EXAMPLE 15

Preparation of 1-p-tolyl 1-methylaminocarbonyl 2-dimethylaminomethyl cyclopropane (Z) hydrochloride In a manner similar to that described in Example 1, but hydrolyzing 1-p-toluyl 1-ethoxycarbonyl 2-dimethylaminomethyl cyclopropane (Z) and then treating the intermediate acid chloride with dimethylamine and salifying by hydrochloric acid, there is obtained the product of the formula

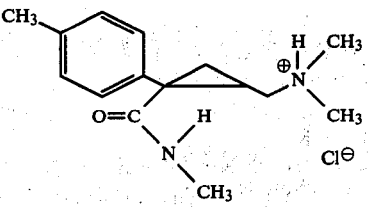

Empirical formula: $C_{15}H_{23}ClN_2O$
Molecular weight: 282.8

EXAMPLE 16

Preparation of 1-p-methoxyphenyl 1-amino methylcarbonyl 2-aminomethyl cyclopropane (Z) hydrochloride In a manner similar to that described in Example 1, but hydrolyzing 1-p-methoxyphenyl 1-ethoxycarbonyl 2-aminomethyl cyclopropane (Z) and then treating the intermediate acid chloride with ammonia and salifying with hydrochloric acid, there is obtained the product of the formula

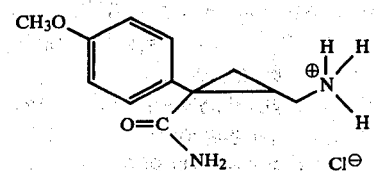

Empirical formula: $C_{12}H_{17}ClN_2O_2$
Molecular weight: 256.7

EXPERIMENTS

(a) Toxicology

The chemical compounds described above were subjected to a toxicity study.
This study was carried out on the conventional mouse weighing from 20 to 22 g.

The substances were administered orally.

The LD$_{50}$ is calculated in accordance with the method of KARBER, Arch. Exptl. Pathol. Pharmacol. 1931, 162, 480.

All the LD$_{50}$s observed are between 300 and 1000 mg/kg.

(b) Pharmacological Study

The pharmacological studies to which the chemical molecules forming the object of the present invention were subjected made it possible to show an anti-depressant activity.

By way of specific example mention may be made of the compound of Example 4, the hydrochloride of 1-phenyl 1-diethylaminocarbonyl 2-aminomethyl cyclopropane (Z) which has an ED$_{50}$ of 0.1 mg/kg in the potentialization test on the toxicity of yohimbine, while the desimipramine used as reference has a reference of ED$_{50}$ of 1.6 mg/kg.

(c) Therapeutic Application

On basis of their pharmacological properties and their low toxicity these compounds can be used in therapy in the treatment of various disturbances of the central nervous system; the compound of Example 4, 1-phenyl 1-diethylaminocarbonyl 2-aminomethyl cyclopropane (Z) hydrochloride, having given particularly interesting results.

The compounds of general formula I of the present invention and their addition salts with therapeutically compatible acids can also be used as drugs, for instance in the form of adapted pharmaceutical preparations which facilitate bioavailability. These preparations may be in solid form, for instance in the form of tablets, pills, capsules or ampules or in liquid form, for example solutions, suspensions or emulsions. The pharmaceutical preparations in a form suitable for injection are subjected to conventional pharmaceutical operations such as sterilization and/or may contain adjuvants, for instance preservatives, stabilizers, wetting or emulsifying agents, buffer tablets, etc.

The doses in which the active compounds and their addition salts can be administered may vary in wide proportions depending on the condition of the patient. A daily dose of about 0.1 mg to 1 mg/kg of body weight is, however, preferred.

The pharmaceutical compositions of the invention can be used in human and veterinary medicine and more particularly in the treatment of neurotic and reactional depressive conditions of various natures.

Of course, the present invention is not limited to the particular examples which have been mentioned merely by way of illustration, but it is entirely possible to think of a number of variants and modifications thereof without thereby going beyond the scope of the invention.

We claim:

1. A 1-aryl 2-aminomethyl cyclopropane carboxamide (Z) of the formula I:

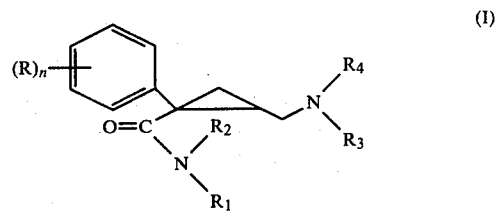

in which:
R represents hydrogen, halogen, lower alkyl, lower alkoxy, hydroxy, nitro, or amino;
n represents the value 1 or 2; $R_1$ and $R_2$ are independently selected from the group consisting of hydrogen, lower alkyl, lower aryl, and lower-alkylaryl, which aryl or alkylaryl group is optionally substituted by a halogen atom, and, with the adjacent nitrogen atom, a heterocycle of 5 or 6 ring members;
$R_3$ and $R_4$ are independently selected from the group consisting of hydrogen, lower alkyl, and, together with the adjacent nitrogen atom, a heterocycle of 5 or 6 ring members optionally containing an additional nitrogen or oxygen heteroatom, or a salt thereof with a therapeutically-acceptable inorganic or organic acid.

2. A compound of claim 1, selected from the group consisting of:
-1-phenyl 1-aminocarbonyl 2-dimethylaminomethyl cyclopropane (Z);
-1-phenyl 1-dimethylaminocarbonyl 2-dimethylaminomethyl cyclopropane (Z);
-1-phenyl 1-ethylaminocarbonyl 2-dimethylaminomethyl cyclopropane (Z) maleate;
-1-phenyl 1-diethylaminocarbonyl 2-aminomethyl cyclopropane (Z) hydrochloride;
-1-phenyl 2-dimethylaminomethyl N-(4'-chlorophenyl)-cyclopropane carboxamide (Z) hydrochloride;
-1-phenyl 2-dimethylaminomethyl N-(4'-chlorobenzyl)-cyclopropane carboxamide (Z) maleate;
-1-phenyl 2-dimethylaminomethyl N-(2-phenylethyl)-cyclopropane carboxamide (Z) hydrochloride;
-(3,4-dichloro-1-phenyl) 2-dimethylaminomethyl N,N-dimethylcyclopropane carboxamide (Z) hydrochloride;
-1-phenyl 1-pyrrolidinocarbonyl 2-morpholinomethyl cyclopropane (Z) hydrochloride;
-1-p-chlorophenyl 1-aminocarbonyl 2-aminomethyl cyclopropane (Z) hydrochloride;
-1-orthochlorophenyl 1-aminocarbonyl 2-dimethylaminomethyl cyclopropane (Z) hydrochloride;
-1-p-hydroxyphenyl 1-aminocarbonyl 2-dimethylaminomethyl cyclopropane (Z) hydrochloride;
-1-p-nitrophenyl 1-dimethylaminocarbonyl 2-dimethylaminomethyl cyclopropane (Z) hydrochloride;
-1-p-aminophenyl 1-dimethylaminocarbonyl 2-dimethylaminomethyl cyclopropane (Z) hydrochloride;
-1-p-tolyl 1-methylaminocarbonyl 2-dimethylaminomethyl cyclopropane (Z) hydrochloride, and
-1-p-methoxyphenyl 1-aminomethylcarbonyl 2-aminomethyl cyclopropane (Z) hydrochloride.

3. A compound of claim 1 wherein one of $R_1$ and $R_2$ is chlorolower-aryl or chlorolower-alkylaryl.

4. A compound of claim 3 wherein a chloro atom is in para position on said aryl ring.

5. A compound of claim 1 wherein R is selected from the group consisiting of halo, amino, nitro, lower-alkyl, lower-alkoxy, and hydroxy; $R_1$ and $R_2$ are independently selected from the group consisting of hydrogen and lower-alkyl; and $R_3$ and $R_4$ are independently selected from the group consisting of hydrogen and lower-alkyl, or a pharmaceutically-acceptable acid addition salt thereof.

6. A compound of claim 5 wherein both $R_1$ and $R_2$ are lower-alkyl.

7. A compound of claim 6 which is 1-phenyl 1-diethylaminocarbonyl 2-aminomethyl cyclopropane (Z) hydrochloride.

8. A pharmaceutical composition, useful in the alleviation of depressions, comprising an effective antidepressant amount of a compound of claim 5 in admixture with a pharmaceutically-acceptable diluent or carrier.

9. A composition of claim 8 wherein both $R_1$ and $R_2$ are lower-alkyl.

10. Composition of claim 9, wherein the compound is 1-phenyl 1-diethylaminocarbonyl 2-aminomethyl cyclopropane (Z) hydrochloride.

11. A pharmaceutical composition, useful in the alleviation of depressions, comprising an effective antidepressant amount of a compound according to claim 1 or 2 together with a pharmaceutically-acceptable diluent or carrier.

12. A method of alleviating depression comprising administering to a subject, suffering from depression, an effective anti-depressive amount of a compound which is a 1-aryl 2-aminomethyl cyclopropane carboxamide (Z) of the formula I:

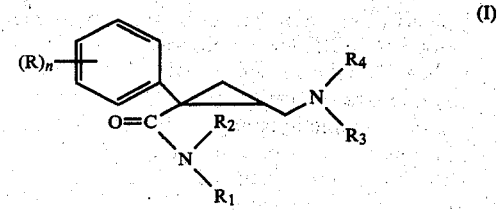

in which:
R represents hydrogen, halogen, loweralkyl, lower alkoxy, hydroxy, nitro, or amino;
n represents the value 1 or 2;
$R_1$ and $R_2$ are independently selected from the the group consisting of hydrogen, lower alkyl, lower aryl, and lower-alkylaryl, which aryl or alkylaryl group is optionally substituted by a halogen atom, and, with the adjacent nitrogen atom, a heterocycle of 5 or 6 ring members;
$R_3$ and $R_4$ are independently selected from the group consisting of hydrogen, lower alkyl, and, together with the adjacent nitrogen atom, a heterocycle of 5 or 6 ring members optionally containing an additional nitrogen or oxygen heteroatom, or a salt thereof with a therapeutically-acceptable inorganic or organic acid.

13. The method of claim 12 wherein the anti-depressive compound is selected from the group consisting of
-1-phenyl 1-aminocarbonyl 2-dimethylaminomethyl cyclopropane (Z);

-1-phenyl 1-dimethylaminocarbonyl 2-dimethylaminomethyl cyclopropane (Z);
-1-phenyl 1-ethylaminocarbonyl 2-dimethylaminomethyl cyclopropane (Z) maleate;
-1-phenyl 1-diethylaminocarbonyl 2-aminomethyl cyclopropane (Z) hydrochloride;
-1-phenyl 2-dimethylaminomethyl N-(4'-chlorophenyl) cyclopropane carboxamide (Z) hydrochloride;
-1-phenyl 2-dimethylaminomethyl N-(4'-chlorobenzyl) cyclopropane carboxamide (Z) maleate;
-1-phenyl 2-dimethylaminomethyl N-(2-phenylethyl) cyclopropane carboxamide (Z) hydrochloride;
-(3,4-dichloro-1-phenyl) 2-dimethylaminomethyl N,N-dimethylcyclopropane carboxamide (Z) hydrochloride;
-1-phenyl 1-pyrrolidinocarbonyl 2-morpholinomethyl cyclopropane (Z) hydrochloride;
-1-p-chlorophenyl 1-aminocarbonyl 2-aminomethyl cyclopropane (Z) hydrochloride;
-1-orthochlorophenyl 1-aminocarbonyl 2-dimethylaminomethyl cyclopropane (Z) hydrochloride;
-1-p-hydroxyphenyl 1-aminocarbonyl 2-dimethylaminomethyl cyclopropane (Z) hydrochloride;
-1-p-nitrophenyl 1-dimethylaminocarbonyl 2-dimethylaminomethyl cyclopropane (Z) hydrochloride;
-1-p-aminophenyl 1-dimethylaminocarbonyl 2-dimethylaminomethyl cyclopropane (Z) hydrochloride;
-1-p-tolyl 1-methylaminocarbonyl 2-dimethylaminomethyl cyclopropane (Z) hydrochloride, and
-1-p-methoxyphenyl 1-aminomethylcarbonyl 2-aminomethyl cyclopropane (Z) hydrochloride.

14. A method of alleviating depression comprising administering to a subject, suffering from depression, an effective anti-depressant amount of (a) a compound which is a 1-aryl 2-aminomethyl cyclopropane carboxamide (Z) of the formula I:

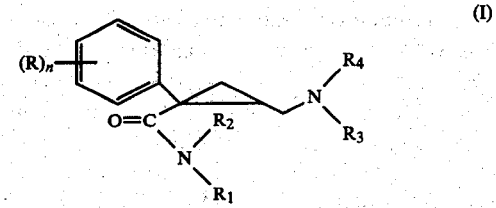

in which:
R represents hydrogen, halogen, loweralkyl, lower alkoxy, hydroxy, nitro, or amino;
n represents the value 1 or 2;
$R_1$ and $R_2$ are independently selected from the the group consisting of hydrogen and lower alkyl;
and wherein $R_3$ and $R_4$ are independently selected from the group consisting of hydrogen and lower-alkyl, or a salt thereof with a pharmaceutically-acceptable acid addition salt, or of (b) a pharmaceutical composition of such a compound together with a pharmaceutically-acceptable carrier.

15. The method of claim 14 wherein both $R_1$ and $R_2$ are lower-alkyl.

16. Method of claim 15, wherein the compound is 1-phenyl-1-diethylaminocarbonyl 2-aminomethyl cyclopropane (Z) hydrochloride.

* * * * *